(12) United States Patent
Blank et al.

(10) Patent No.: US 7,509,153 B2
(45) Date of Patent: *Mar. 24, 2009

(54) METHOD AND APPARATUS FOR CONTROL OF SKIN PERFUSION FOR INDIRECT GLUCOSE MEASUREMENT

(75) Inventors: Thomas B. Blank, Gilbert, AZ (US);
Timothy L. Ruchti, Gilbert, AZ (US);
Mutua Mattu, Chandler, AZ (US);
Marcy Makarewicz, Tempe, AZ (US);
Stephen L. Monfre, Gilbert, AZ (US);
Alexander D. Lorenz, Chandler, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 429 days.

This patent is subject to a terminal disclaimer.

(21) Appl. No.: 10/384,049

(22) Filed: Mar. 7, 2003

(65) Prior Publication Data

US 2004/0039271 A1 Feb. 26, 2004
US 2008/0200783 A9 Aug. 21, 2008

Related U.S. Application Data

(63) Continuation-in-part of application No. 10/349,573, filed on Jan. 22, 2003, now Pat. No. 7,039,446, and a continuation-in-part of application No. 09/955,531, filed on Sep. 17, 2001, now Pat. No. 6,640,117.

(60) Provisional application No. 60/363,345, filed on Mar. 8, 2002, provisional application No. 60/235,369, filed on Sep. 26, 2000.

(51) Int. Cl.
*A61B 5/1455* (2006.01)
(52) U.S. Cl. ...................... 600/310; 600/316

(58) Field of Classification Search ............... 600/322, 600/316, 334
See application file for complete search history.

(56) References Cited

U.S. PATENT DOCUMENTS 5,007,423 A * 4/1991 Branstetter et al. .......... 600/334

(Continued)

FOREIGN PATENT DOCUMENTS

WO WO99/59464 A1 11/1999

(Continued)

OTHER PUBLICATIONS

Helwig, AM; Arnold, MA; Small, GW; Evaluation of Kromoscopy: Resolution of glucose and urea, Applied Optics 2000 39, 4715-4720.*

(Continued)

*Primary Examiner*—Eric F Winakur
(74) *Attorney, Agent, or Firm*—Michael A. Glenn; Glenn Patent Group (57) ABSTRACT

A method and apparatus for noninvasive glucose measurement measures glucose indirectly from the natural response of tissue to variations in analyte concentration. The indirect measurement method utilizes factors affected by or correlated with the concentration of glucose, such as refractive index, electrolyte distribution or tissue scattering. Measurement reliability is greatly improved by stabilizing optical properties of the tissue at the measurement site, thus blood perfusion rates at the sample site are regulated. Perfusion is monitored and stabilized by spectroscopically measuring a control parameter, such as skin temperature, that directly affects perfusion. The control parameter is maintained in a range about a set point, thus stabilizing perfusion. Skin temperature is controlled using a variety of means, including the use of active heating and cooling elements, passive devices, such as thermal wraps, and through the use of a heated coupling medium having favorable heat transfer properties.

17 Claims, 3 Drawing Sheets

U.S. PATENT DOCUMENTS

| | | | | |
|---|---|---|---|---|
| 5,153,368 | A | * | 10/1992 | Fogle, Jr. .................. 102/202.2 |
| 5,402,777 | A | * | 4/1995 | Warring et al. .............. 604/307 |
| 5,487,384 | A | * | 1/1996 | Lee ............................. 600/316 |
| 5,551,422 | A | * | 9/1996 | Simonsen et al. ........... 600/322 |
| 5,615,672 | A | * | 4/1997 | Braig et al. .................. 600/474 |
| 5,876,121 | A | * | 3/1999 | Burns et al. ..................... 356/43 |
| 6,002,597 | A | * | 12/1999 | Rozman .................. 363/21.06 |
| 6,002,953 | A | * | 12/1999 | Block .......................... 600/316 |
| 6,025,597 | A | * | 2/2000 | Sterling et al. ........... 250/341.6 |
| 6,044,285 | A | * | 3/2000 | Chaiken et al. ............. 600/316 |
| 6,049,727 | A | * | 4/2000 | Crothall ...................... 600/310 |
| 6,049,728 | A | * | 4/2000 | Chou .......................... 600/316 |
| 6,072,180 | A | * | 6/2000 | Kramer et al. ........... 250/341.6 |
| 6,119,026 | A | * | 9/2000 | McNulty et al. ............. 600/310 |
| 6,125,297 | A | * | 9/2000 | Siconolfi ..................... 600/547 |
| 6,152,876 | A | | 11/2000 | Robinson et al. |
| 6,161,028 | A | * | 12/2000 | Braig et al. .................. 600/316 |
| 6,216,022 | B1 | * | 4/2001 | Tyrrell et al. ................. 600/310 |
| 6,240,306 | B1 | | 5/2001 | Rohrscheib et al. |
| 6,241,663 | B1 | * | 6/2001 | Wu et al. ..................... 600/322 |
| 6,280,381 | B1 | * | 8/2001 | Malin et al. ................... 600/322 |
| 6,309,884 | B1 | * | 10/2001 | Cooper et al. ............... 600/316 |
| 6,377,828 | B1 | * | 4/2002 | Chaiken et al. ............. 600/316 |
| 6,466,808 | B1 | * | 10/2002 | Chin et al. ................... 600/323 |

FOREIGN PATENT DOCUMENTS

WO        WO 01/28417 A1      4/2001

OTHER PUBLICATIONS

Heise HM, Marbach R, Koshinsky TH, Gries FA. "Non-invasive blood glucose sensors based on near-infrared spectroscopy," Artif Org 1994;18:439-47.*

T.B. Blank, T.L. Ruchti, S.F. Malin and S.L. Monfre, "The use of near-infrared diffuse reflectance for the non-invasive prediction of blood glucose," IEEE Lasers and electro-optics society newsletter, vol. 13, No. 5, Oct. 1999.*

Jagemann KU, Fischbacker C, Danzer K, Muller UA, Merters B. "Application of near-infrared spectroscopy for non-invasive determination of blood/tissue glucose using neural network," Z Phys Chem 1995;191S:179-190.*

Robinson MR, Eaton RP, Haaland DM, Keep GW, Thomas EV, Stalled BR, Robinson PL. "Non-invasive glucose monitoring in diabetic patients: A preliminary evaluation," Clin Chem 1992;38:1618-22.*

Klonoff, D.C., "Mid-Infrared Spectroscopy for Noinvasive Blood Glucose Monitoring," IEEE Lasers and electro-optics society newsletter, vol. 12, No. 2, Apr. 1998.*

P. Zheng, P., C.E. Kramer, C.W. Barnes, J.r. Braig, B.B. Sterling, "Noninvasive Glucose Determination by Oscillating Thermal Gradient Spectrometry," Diabetes Technology & Therapeutics, vol. 2, No. 1, pp. 17-25, 2000.*

Shichiri, M., T. Uemura, K. Nishida, "Non-invasive Fourier Transformed Infrared Spectroscopy for the Measurement of Submucosal Tissue Glucose Concentration," IEEE Lasers and electro-optics society newsletter, vol. 12, No. 2, Apr. 1998.*

Bittner, A., H.M. Heise, Th. Koschinsky, F.A. Gries, "Evaluation of Microdialysis and FT-IR ATR-spectroscopy for in-vivo Blood Glucose Monitoring," Mikrochim. Acta [suppl.] 14. 827-828 (1997).*

Khalil OS. "Spectroscopic and clinical aspects of non-invasive measurments," Clin Chem 1999;45:165-77.*

S.Y. Wang, C.E. Hasty, P.A. Watson, J.P. Wickstead, R.D. Stith and W.F. March, "Analysis of Metabolites in Aqueous Solutions Using Laser Raman Spectroscopy," Applied Optics, vol. 32, No. 6, pp. 925-929.*

Cote, G.L., "Noninvasive Optical Glucose Sensing--An Overview," J. Clin. Eng., pp. 253-259, Jul./Aug. 1997.*

Waynant, R.W. and V.M. Chenault, "Overview of Non-Invasive Fluid Glucose Measurement Using Optical Techniques to Maintain Glucose Control in Diabetes Mellitus," IEEE Lasers and electro-optics society newsletter, vol. 12, No. 2, Apr. 1998.*

Heise, H.M., "Near-Infrared Spectrometry for in vivo Glucose Sensing," in Biosensors in the Body: Continuous in vivo Monitoring, Ed. D.M. Fraser: John Wiley & Sons, 1997.*

Bruulsema, J.T et al., "Correlation between blood glucose concentration in diabetics and noninvasively measured tissue optical scattering coefficient," Optics Letters, vol. 22, No. 3, Feb. 1, 1997, pp. 182-190.*

Diabetes Statistics. Bethesda, MD: National Institute of Health, Publication No. 98-3926, Nov. 1997.

The Diabetes Control and Complications Trial Research Group. The effect of intensive treatment of diabetes on the development and progression of long-term complications in insulin-dependent diabetes mellitus. N Eng J of Med 1993;329:977-86.

U.K. Prospective Diabetes Study (UKPDS) Group, "Intensive blood-glucose control with sulphonylureas or insulin compared with conventional treatment and risk of complications in patients with type 2 diabetes," Lancet, vol. 352, pp. 837-853, 1998.

Ohkubo, Y., H. Kishikawa, E. Araki, T. Miyata, S. Isami, S. Motoyoshi, Y. Kojima, N. Furuyoshi, and M. Shichizi, "Intensive insulin therapy prevents the progression of diabetic microvascular complications in Japanese patients with non-insulin-dependent diabetes mellitus: a randomized prospective 6-year study," Diabetes Res Clin Pract vol. 28 No. 103-117 1995.

Tamada, J.A., S. Garg, L. Jovanovic, K.R. Pitzer, S. Fermi, R.O. Potts, "Noninvasive Glucose Monitoring Comprehensive Clinical Results," JAMA, vol. 282, No. 19, pp. 1839-1844, Nov. 17, 1999.

Gross, T.M., B.W. Bode, D. Einhorn, D.M. Kayne, J.H. Reed, N.H. White and J.J. Mastrototaro, "Performance Evaluation of the MiniMed" Continuous Glucose Monitoring System During Patient Home Use, Diabetes Technology & Therapeutics, vol. 2, No. 1, 2000.

Hazen, Kevin H. "Glucose Determination in Biological Matrices Using Near-Infrared Spectroscopy", doctoral dissertation, University of Iowa, 1995.

Jungheim, Karsten; Koschinsky, Theodor "Glucose Monitoring at the Arm", Diabetes Care, 25, 2002, 956-960.

Jungheim, Karsten; Koschinsky, Theodor "Risky Delay of Hypoglycemia Detection by Glucose Monitoring at the Arm", Diabetes Care, 24, 2001, 1303-1304.

Fischer, Jerome S.; Hazen, Kevin H.; Welch, Matthew; Hockersmith, Linda; Coates, Jennifer "Comparisons of Capillary Blood Glucose Concentrations from the Fingertips and the Volar Aspects of the Left and Right Forearms", American Diabetes Assn, 62nd Annual Meeting, Jun. 14, 2002.

McGarraugh, Geoff; Schwartz, Sherwyn; Weinstein, Richard "Glucose Measurements Using Blood Extracted from the Forearm and the Finger", TheraSense, Inc., ART01022 Rev. C, 2001.

McGarraugh, Geoff; Price, David; Schwartz, Sherwyn; Weinstein, Richard "Physiological Influences on Off-Finger Glucose Testing", Diabetes Technology & Therapeutics, 3, 2001, 367-376.

Ryan, T.J. "A Study of the Epidermal Capillary Unit in Psoriasis", Dermatologica, 1969, 138, 459-472.

Ng, Ron Presentation to the FDA at the Clinical Chemistry & Clinical Toxicology Devices Panel Meeting, Gaithersburg, MD Oct. 29, 2001.

* cited by examiner

METHOD AND APPARATUS FOR CONTROL OF SKIN PERFUSION FOR INDIRECT GLUCOSE MEASUREMENT

CROSS REFERENCE TO RELATED APPLICATIONS

This application claims benefit of U.S. Provisional Patent Application Ser. No. 60/363,345, filed Mar. 8, 2002; and is a Continuation-in-part of U.S. Pat. No. 6,640,117 granted Oct. 28, 2003 (U.S. patent application Ser. No. 09/955,531, filed Sep. 17, 2001), which claims benefit of U.S. Provisional Patent Application Ser. No. 60/235,369, filed Sep. 26, 2000 and is a Continuation-in-part of U.S. Pat. No. 7,039,446 granted May 2, 2006 (U.S. patent application Ser. No. 10/349,573 filed Jan. 22, 2003).

BACKGROUND OF THE INVENTION

1. Field of the Invention

This invention relates generally to the field of noninvasive glucose measurement. More particularly, the invention relates to control of optical properties of the sampling site to improve reliability of a noninvasive glucose measurement.

2. Background Information

Diabetes is a chronic disease involving the improper production and utilization of insulin, a hormone that facilitates glucose uptake into cells. While a precise cause of diabetes is unknown, both genetic and environmental factors such as obesity and lack of exercise appear to play roles. Persons with diabetes have increased health risk in three broad categories: cardiovascular heart disease, retinopathy, and neuropathy. Potential disease complications include heart disease and stroke, high blood pressure, kidney disease, neuropathy, retinopathy, diabetic ketoacidosis, skin conditions, gum disease, impotence, and fetal complications.

Diabetes Prevalence and Trends

The incidence of diabetes is both common and on the increase, making the disease a leading cause of death and disability worldwide. The World Health Organization (WHO) estimates that diabetes currently afflicts one hundred fifty-four million people worldwide. Fifty-four million people with diabetes live in developed countries. The WHO estimates that the incidence of diabetes will grow to three hundred million by the year 2025. In the United States, 15.7 million people or 5.9% of the population are estimated to have diabetes. Within the United States, the prevalence of adults diagnosed with diabetes increased by six percent in 1999 and rose by thirty-three percent between 1990 and 1998. This corresponds to approximately eight hundred thousand new cases every year in America. The estimated total cost to the United States economy exceeds $90 billion per year. National Institutes of Health, *Diabetes Statistics*, Publication No. 98-3926, Bethesda Md. (1997).

Long-term clinical studies show that the onset of diabetes related complications can be significantly reduced through proper control of blood glucose levels. The Diabetes Control and Complications Trial Research Group, *The effect of intensive treatment of diabetes on the development and progression of long-term complications in insulin-dependent diabetes mellitus*, N Eng J of Med, 329:977–86 (1993); and 1 U.K. Prospective Diabetes Study (UKPDS) Group, *Intensive blood-glucose control with sulphonylureas or insulin compared with conventional treatment and risk of complications in patients with type 2 diabetes*, Lancet, 352:837–853 (1998); and 1 Y. Ohkubo, H. Kishikawa, E. Araki, T. Miyata, S. Isami, S. Motoyoshi, Y. Kojima, N. Furuyoshi, M. Shichizi, *Intensive insulin therapy prevents the progression of diabetic microvascular complications in Japanese patients with non-insulin-dependent diabetes mellitus: a randomized prospective 6-year study*, Diabetes Res Clin Pract, 28:103–117 (1995).

A vital element of diabetes management is the self-monitoring of blood glucose levels in the home environment. However, current monitoring techniques discourage regular use due to the inconvenient and painful nature of drawing blood through the skin prior to analysis. See The Diabetes Control and Complication Trial Research Group, supra. As a result, noninvasive measurement of glucose has been identified as a beneficial development for the management of diabetes. Implantable glucose analyzers eventually coupled to an insulin delivery system providing an artificial pancreas are also being pursued.

Glucose Measurement: History, Approaches, and Technologies

The treatment of diabetes has progressed through several stages. The combined development of insulin therapy and the development of devices for the self-monitoring of blood glucose in the home led to a radical improvement in the lives of individuals afflicted with diabetes. Self-monitoring of blood glucose has progressed through multiple stages from early testing that used urine samples to the current standard of invasive finger stick samples that are more accurate but somewhat painful. The development of alternative site glucose measurement technology has somewhat mitigated the pain aspects, but poses a biohazard. Alternate site blood glucose concentration levels are also known to differ from those taken at the fingertip during periods when glucose concentrations are rapidly changing. The difference is related to circulatory transport of glucose to peripheral tissues: Alternate site tissue sites with lower blood perfusion than the finger will exhibit a delay in the rise and fall of glucose levels when compared with finger blood glucose.

Current research is focused on the development of noninvasive technologies that will totally eliminate the pain associated with glucose determination and fluid biohazard issues. Another important area of research involves the combination of automated glucose measurement and insulin therapy. Progress has been reported in the research on implantable or full-loop systems that have been proposed to incorporate both glucose measurement and control through automated insulin delivery. In the interim, a device that provides noninvasive, automatic, or (nearly) continuous measurement of glucose levels would clearly be useful to those afflicted with diabetes. Various systems have been developed with this goal in mind. J. Tamada, S. Garg, L. Jovanovic, K. Pitzer, S. Fermi, R Potts, *Noninvasive glucose monitoring comprehensive clinical results*, JAMA, 282:1839–1844 (1999) describe a minimally-invasive monitoring system reported that provides three readings of interstitial fluid glucose per hour, each delayed by up to fifteen minutes due to the sample acquisition process. The measurement is made through an electrochemical-enzymatic sensor on a sample of interstitial fluid that is drawn through the skin using an iontophoresis technique. Other approaches, such as the continuous monitoring system reported by T. Gross, B. Bode, D. Einhorn, D. Kayne, J. Reed, N. White and J. Mastrototaro, *Performance evaluation of the Minimed® continuous glucose monitoring system during patient home use*, Diabetes Technology & Therapeutics, Vol. 2, Num. 1, (2000) involve the surgical implantation of a sensor in tissue. Health risks due to sensor implantation or measurement delay remain as obstacles to efficacious use of these devices in directing insulin therapy. To date, a fully noninvasive alternative has not been approved by the FDA.

Noninvasive Glucose Measurement

There exist a number of noninvasive approaches for glucose determination. These approaches vary widely, but have at least two common steps. First, an apparatus is utilized to acquire a reading from the body without obtaining a biological sample. Second, an algorithm is utilized to convert this reading into a glucose determination.

A generalized approach to noninvasive glucose measurement utilizes some form of spectroscopy to acquire the signal or spectrum from a measurement site on the subject's body. Techniques include but are not limited to: impedance, Raman, and fluorescence; as well as techniques using light, from the ultraviolet through the infrared [ultraviolet (200 to 400 nm), visible (400 to 700 nm), near-IR (700 to 2500 nm or 14,286 to 4000 $cm^{-1}$), infrared (2500 to 14,285 nm or 4000–700 $cm^{-1}$)]. A specific near infrared range for noninvasive glucose determination in diffuse reflectance mode is about 1100 to 2500 nm or ranges or sets of ranges therein. K. Hazen, *Glucose Determination in Biological Matrices Using Near-infrared Spectroscopy*, doctoral dissertation, University of Iowa (1995). It is important to note, that these techniques are distinct from the minimally invasive techniques listed above in that the sample analyzed is a portion of the human body in situ, not a biological sample extracted from the human body.

Potential sites for the noninvasive measurement have been identified from the ear lobe, oral mucosa, arm, and eye to the fingertip. It is important to note that noninvasive techniques do not have to be based upon spectroscopy. Within the context of the invention, any device that reads glucose from the body without penetrating the skin and collecting a biological sample is classified as a noninvasive glucose analyzer.

To date, noninvasive glucose measurement has conventionally employed a direct measurement approach, in which the net analyte signal due to the absorption of light by glucose in the tissue is used to calculate the glucose concentration. There exist formidable challenges to the development of reliable methods of glucose measurement using a direct approach. Among these challenges are the size of the glucose signal relative to the spectral background, the heterogeneity of the sample, the multi-layered structure of the skin, the rapid variation related to hydration levels, changes in the volume fraction of blood in the tissue, hormonal stimulation, temperature fluctuations, and blood analyte levels. Control of the optical properties of the sample site is essential to the success of any method of noninvasive glucose measurement using a direct measurement approach.

Calibration And Utilization Of Noninvasive Glucose Meters

One noninvasive technology, near-infrared spectroscopy, provides the opportunity for both frequent and painless noninvasive measurement of glucose. This approach involves the illumination of a spot on the body with near-infrared (NIR) electromagnetic radiation, light in the wavelength range 700 to 2500 nm. The light is partially absorbed and scattered, according to its interaction with the constituents of the tissue. The actual tissue volume that is sampled is the portion of irradiated tissue from which light is collected and transported to the spectrometer detection system.

Generation of a suitable calibration involves development of a mathematical relationship between an in vivo near-infrared spectral measurement and a corresponding reference blood glucose concentration. The model generation process includes the collection of a multiplicity of matched spectrum/reference glucose pairs followed by the calculation of a regression model between the multiple independent variables contained in each spectral vector and the associated single dependent reference glucose value. Reference blood glucose values are typically obtained directly through the use of measurement tools like the HEMOCUE (YSI, Inc., Yellow Springs Ohio) or any other reliable invasive glucose analyzer.

The Beer-Lambert Law, equation 1 infra, defines a proportionality constant between glucose concentration and spectral light absorbed at a single spectral wavelength in the special case where no interfering spectral signatures are present. In equation 1, A is the scalar absorbance measurement at a given wavelength of light, $\epsilon$ is the molar absorptivity associated with the molecule of interest at the same given wavelength, b is the distance (or pathlength) that the light travels through the sample, and C is the concentration of the molecule of interest (glucose).

$$A = \epsilon b C$$

A number of interferences do exist for the near-infrared measurement making the correction for these interferences necessary. Correction is achieved by using multiple wavelengths in each spectrum in a multivariate regression model. Such a model is proven means for compensation of spectral interferences, requiring some measure of uniqueness in the spectral signature of the glucose.

$$\mathbf{k} \mathbf{A} = C$$

In equation 2, boldface type denotes vector variables. The expression is interpreted as the outer product of the regression vector k and the absorbance spectrum vector A, consisting of the absorbance at a multiplicity of selected wavelengths, is equal to the glucose concentration C of the sample.

Common multivariate approaches that can be used to solve the equation 2 for the regression vector k can include partial least squares (PLS) and principal component regression (PCR). Nonparametric methods of calibration such as neural networks and multiple adaptive regression splines (MARS) can also be used to model an expression analogous to equation 2 in the case where Beer's law deviations are present and the relation becomes nonlinear.

Because every method of glucose measurement has error, it is beneficial that the primary reference device, which is used to develop and evaluate noninvasive calibrations for blood glucose, be as accurate as possible to minimize the uncertainty in the model. An instrument with a percentage error of five or less is most desirable. An instrument having a percentage error of up to ten would be suitable, though the error of the device being calibrated may increase.

Instrumentation

Noninvasive

A number of technologies have been proposed for measuring glucose non-invasively, all of which involve some type of tissue measurement. Spectroscopy-based noninvasive glucose analyzers utilize the measured interaction of the tissue sample with electromagnetic radiation (EMR) or another type of energy input that leads to an emission of EMR to acquire the signal or spectrum. Examples include but are not limited to Nuclear Magnetic Resonance (NMR) spectroscopy, UV, visible near-infrared, mid-infrared, and far-infrared spectroscopy, tissue impedance spectroscopy, Raman spectroscopy, and fluorescence spectroscopy. The near infrared range for noninvasive glucose determination in diffuse reflectance mode is about 1100 to 2500 nm or ranges therein. Hazen (1995), supra. It is important to define noninvasive techniques as being distinct from invasive techniques in that the noninvasive sample is analyzed in-situ, as opposed to invasively extracting a biological sample through the skin for analysis.

The actual tissue volume that is sampled is the portion of irradiated tissue from which light is reflected or transmitted to the spectrometer detection system. All of these techniques share the common characteristic that, as secondary calibration methods, they require a calibration, model or other transformation to convert the measured signal to an estimate of the glucose concentration using reference measurements based on a primary method, such as invasive measurements from samples of venous or capillary blood.

A number of spectrometer configurations exist for collecting noninvasive spectra from regions of the body. Typically a spectrometer has one or more beam paths from a source to a detector. A light source may include a blackbody source, a tungsten-halogen source, one or more LED's, or one or more laser diodes. For multi-wavelength spectrometers a wavelength selection device may be utilized or a series of optical filters may be utilized for wavelength selection. Wavelength selection devices include dispersive elements such as prisms, and gratings of various types. Nondispersive wavelength selective devices include interferometers, successive illumination of the elements of an LED array, and wavelength selective filters. Detectors may be in the form of one or more single element detectors or one or more arrays or bundles of detectors. Detector materials are selected to obtain the desired signal measurement characteristics over the necessary wavelength ranges. Light collection optics such as fiber optics, lenses, and mirrors are commonly utilized in various configurations within a spectrometer to direct light from the source to the detector by way of a sample.

The interface of the glucose analyzer to the tissue includes a patient interface module for directing light into and collecting light from the tissue measurement site. Optical conduits for directing and collecting light may include a light pipe, fiber optics, a focusing lens system, or a light directing mirror system.

The scanning of the tissue can be done continuously when pulsation effects do not affect the tissue area being tested, or the scanning can be done intermittently between pulses. The collected signal (near-infrared radiation in this case) is converted to a voltage and sampled through an analog-to-digital converter for analysis on a microprocessor based system and the result displayed.

Related Skin Physiology

One of the primary functions of cutaneous skin is to provide a means for thermoregulatory control of body temperature. Blood at approximately 98° F. is pumped to the outer skin layers to provide nutrients, is a means for waste removal, and is a mechanism for thermoregulatory control. In the case of warm ambient temperatures, heat can be dissipated from the core of the body when increased blood flow is combined with the cooling effects of sweat evaporation on the skin surface. In the case of cool ambient temperatures, heat can also be used to warm a cool skin surface, but rapid heat loss associated with touching cold objects is limited by constrictively reducing blood flow to the superficial tissues. These thermoregulatory mechanisms typically use constriction or dilation of capillary vessels and the concomitant variation in blood flow to control the potential for heat transfer to and from the body. Capillary diameters can vary tenfold during these processes.

A tenfold variation in capillary vessel diameter can lead to substantial changes in the composition and optical properties of the tissue. Such variation in the measured tissue sample can lead to poor sampling precision over a sequential series of measurements. Sample normalization of a varying signal derived from the heterogeneous, layered structure of skin can be of limited effectiveness due to spectral nonlinearities imposed by the compositional variation of the layers and the sequential path of light through the various layers of skin. Specifically, the broadband source light is filtered uniquely in the wavelength domain by each skin layer according to the changing compositions and varying optical densities that result with a perfusion shift in the tissue. The result is that the optical sample is destabilized in a nonlinear manner that is difficult or impossible to normalize with a high degree of accuracy. It follows that the modeling of glucose concentration will be most efficacious under the conditions that variations in the optical properties of the sample are minimized excepting where changes in the optical properties are a direct result of glucose variation.

Accuracy and robustness are improved with thermal control in the case of either a conventional direct measurement or an indirect measurement, described below, of blood glucose. Thermally or mechanically stimulated changes in optical properties will complicate direct noninvasive glucose determinations. Thermal perturbations are addressed herein using the knowledge of human vascular response to heat and cold and by limiting temperature transients due to skin contact with objects that differ by more than 5 degrees F. from typical resting skin temperatures of 85–95° F.

Description of Related Technology

There are a number of issues related to obtaining representative samples in analytical technologies. Factors affecting sample stability may be environmental or natural physiological variation that can arise from variations in sample site location or time dependent physiologies. Environmental factors, such as temperature, can affect instrumentation, electronics, and physiological components. For example, in near-IR spectroscopy, environmental temperature may affect either or both of the alignment of a spectrometer and the temperature of the probing device, which secondarily affects the tissue temperature upon contact. In the case of noninvasive glucose determination performed via near-IR spectroscopy, the result of these changes is a change in the acquired spectra due to the effect of temperature and pressure on tissue optical properties.

Furthermore, temperature effects the localized perfusion of the tissue. The localized perfusion is important for several reasons. First, vasodilatation of the surface capillaries affects the amount of blood present near the skin surface. This change can effect the glucose concentration in the sampled tissue volume. Second, it has been reported that blood at alternative sites, such as the forearm, can contain glucose concentrations that are dampened and/or delayed versus blood in well perfused areas, such as an artery, vein, or fingertip capillary bed. K. Jungheim, T. Koschinsky, *Glucose Monitoring at the Arm*, Diabetes Care, 25:956–960 (2002); and K. Jungheim, T. Koschinsky, *Risky delay of hypoglycemia detection by glucose monitoring at the arm*, Diabetes Care, 24:1303–1304 (2001); and J. Fischer, K. Hazen, M. Welch, L. Hockersmith, J. Coates, *Comparisons of capillary blood glucose concentrations from the fingertips and the volar aspects of the left and right forearms*, American Diabetes Association, $62^{nd}$ Annual Meeting (Jun. 14, 2002).

A number of approaches have been utilized to minimize this lag. For example, M. Rohrscheib, C. Gardner, M. Robinson, Method and apparatus for noninvasive blood analyte measurement with fluid compartment equilibration, U.S. Pat. No. 6,240,306 (May 29, 2001) suggests applying heat to the skin surface to increase perfusion. The Rohrscheib patent describes elevating localized skin temperature from 35° C. by at least 5° C. and preferably by about 7° C. in order to equilibrate the glucose concentration between the vascular system and skin tissue. The reported mechanism involves the local dilation of capillaries to increase blood flow, which results in a partial equalization of the venous and capillary glucose concentrations. Rohrscheib, et al. further teach use of vasodilating agents such as nicotinic acid, methyl nicotinamide, minoxidil, nitroglycerin, histamine, capsaicin, or menthol to increase local blood flow. While tissue perfusion can be increased to maximal levels though application of thermal energy, it has the additional undesirable effect of destabilizing optical properties of the tissue sample.

A method and apparatus for sample site temperature stabilization in conjunction with near-IR based noninvasive glucose determination has been reported. K. Hazen (1995), supra, pp. 193–249. This method utilizes a heater in thermal contact with the sampling site, but the methodology is for a direct reading of glucose and the temperatures are elevated to above forty degrees centigrade.

There exists therefore a need in the art for a noninvasive method of glucose measurement that overcomes the difficulties inherent in methods based on direct measurement of a net analyte signal. There further exists a need to maximize the reliability of such a method by providing a means for controlling and/or eliminating the fluctuation of optical properties of tissue sample by stabilizing perfusion of the sample site.

SUMMARY OF THE INVENTION

The invention provides methods and a system for noninvasively measuring key constituents and properties of tissue. A target analyte is measured indirectly based on the natural response of tissue to variations in analyte concentration. The indirect method of measuring utilizes factors that are effected by or correlated with the concentration of glucose, such as the index of refraction, electrolyte distribution or reduced scattering coefficient of the bulk tissue. An indirect measurement means that an ancillary effect due to changes in glucose concentration is being measured.

The reliability of the measurement is greatly improved by stabilizing the optical properties of the tissue at the measurement site, thus means are provided for regulating blood perfusion rates at the sample site. In one embodiment, perfusion is monitored and stabilized by spectroscopically measuring a control parameter, such as skin temperature, that directly affects perfusion. The control parameter is maintained in a range about a set point, thus stabilizing perfusion. Skin temperature is controlled using a variety of means, including the use of active heating and cooling elements, passive devices, such as thermal wraps, and through the use of a heated coupling medium having favorable heat transfer properties.

DETAILED DESCRIPTION

Indirect Measurement

A method for indirectly determining a concentration of a target analyte, such as glucose, noninvasively is described in the commonly-assigned U.S. patent application Ser. No. 10/349,573 (filed Jan. 22, 2003), the entirety of which is hereby incorporated by reference as if fully set forth herein. The method takes advantage of the fact that tissue properties are responsive to and reflect physiological variations in the tissue related to variations in the concentration of analyte. An analytical signal is collected at a sampling site on a subject's body. Features are extracted from the analytical signals that are indicative of the target analyte on the sampled tissue. Feature extraction is any mathematical transformation that enhances a quality or aspect of the sample measurement for interpretation. The general purpose of feature extraction is to concisely represent or enhance any of the structural, chemical physiological, and optical properties of the tissue measurement site that are indirectly related to the target analyte. Analyte concentration is calculated indirectly by applying a calibration model to the features. The extracted features are reflective of changes in tissue properties, which themselves are responsive to and reflect physiological variations in the tissue related to variations in the concentration of analyte. Thus, indirect measurement measures a target analyte by measuring an ancillary effect of the target analyte.

Figure 1:
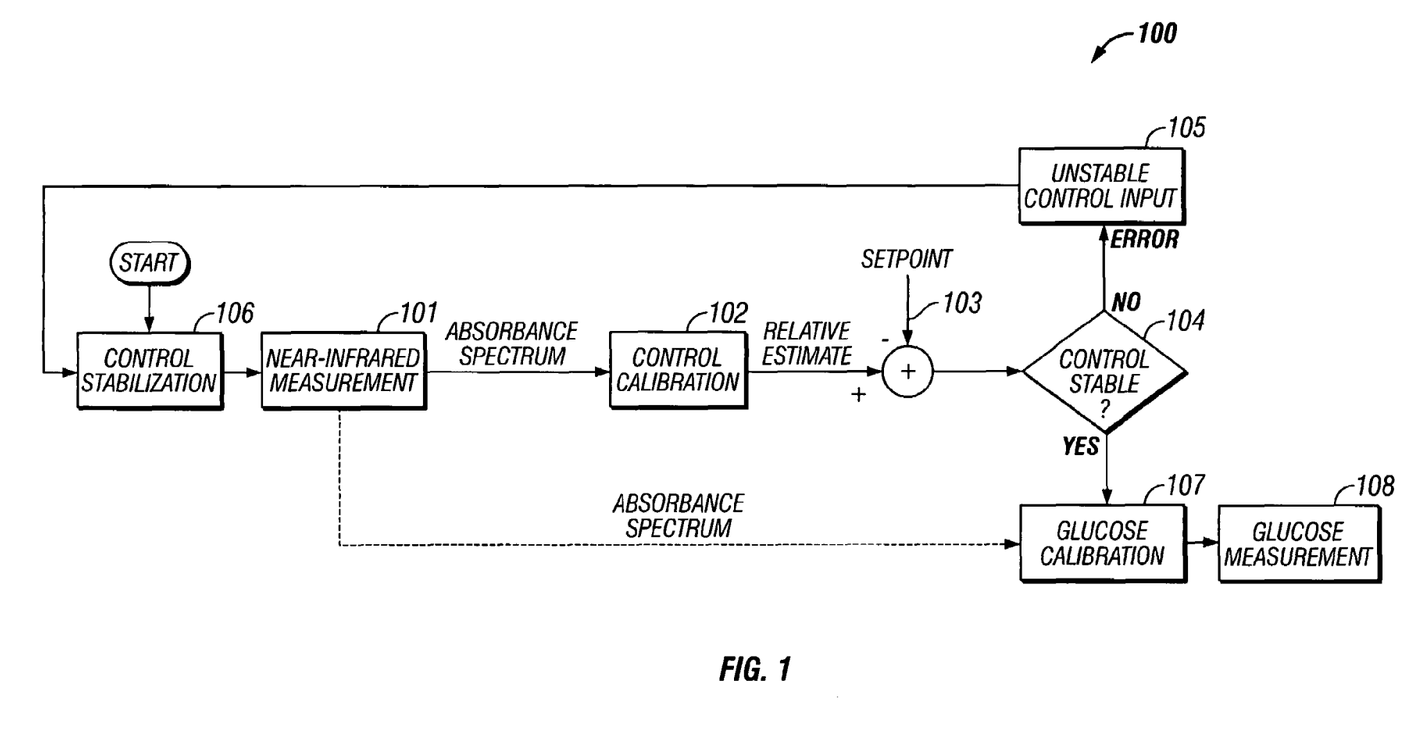
FIG. 1 provides a flow diagram of a method for regulating a control parameter at a tissue measurement site according to the invention.

The invention provides a method and apparatus of noninvasive glucose measurement in which blood perfusion at the sample site is regulated through regulation of a control parameter that directly influences perfusion, such as skin temperature. FIG. 1 shows a flow diagram of a method for noninvasive glucose determination that includes perfusion control at the sample site. As shown in FIG. 1, perfusion is controlled through the provision of a feedback loop that maintains the control parameter within an acceptable range about a set point. For example, blood perfusion increases rapidly and is volatile above skin temperatures of 40° C., thus it is desirable to regulate skin temperature at the sampling site to a range between approximately 30 and 40° C.; preferably the skin temperature is controlled between 30 and 35° C. More preferably, the skin is controlled to within one degree of a control set-point in a range of 30 to 35° C. The control set point is established by the environmental conditions and the patient physiology at the time of a periodic instrument bias correction. Notably, only the outermost 100 μm of skin temperature need be controlled, as below this depth the capillary bed controls the skin temperature. While the invention specifically provides a method of indirect measurement as described above, the principle of controlling blood perfusion is also readily applied to noninvasive measurement approaches in which analyte concentration is directly determined based on the net analyte signal.

Figure 3:
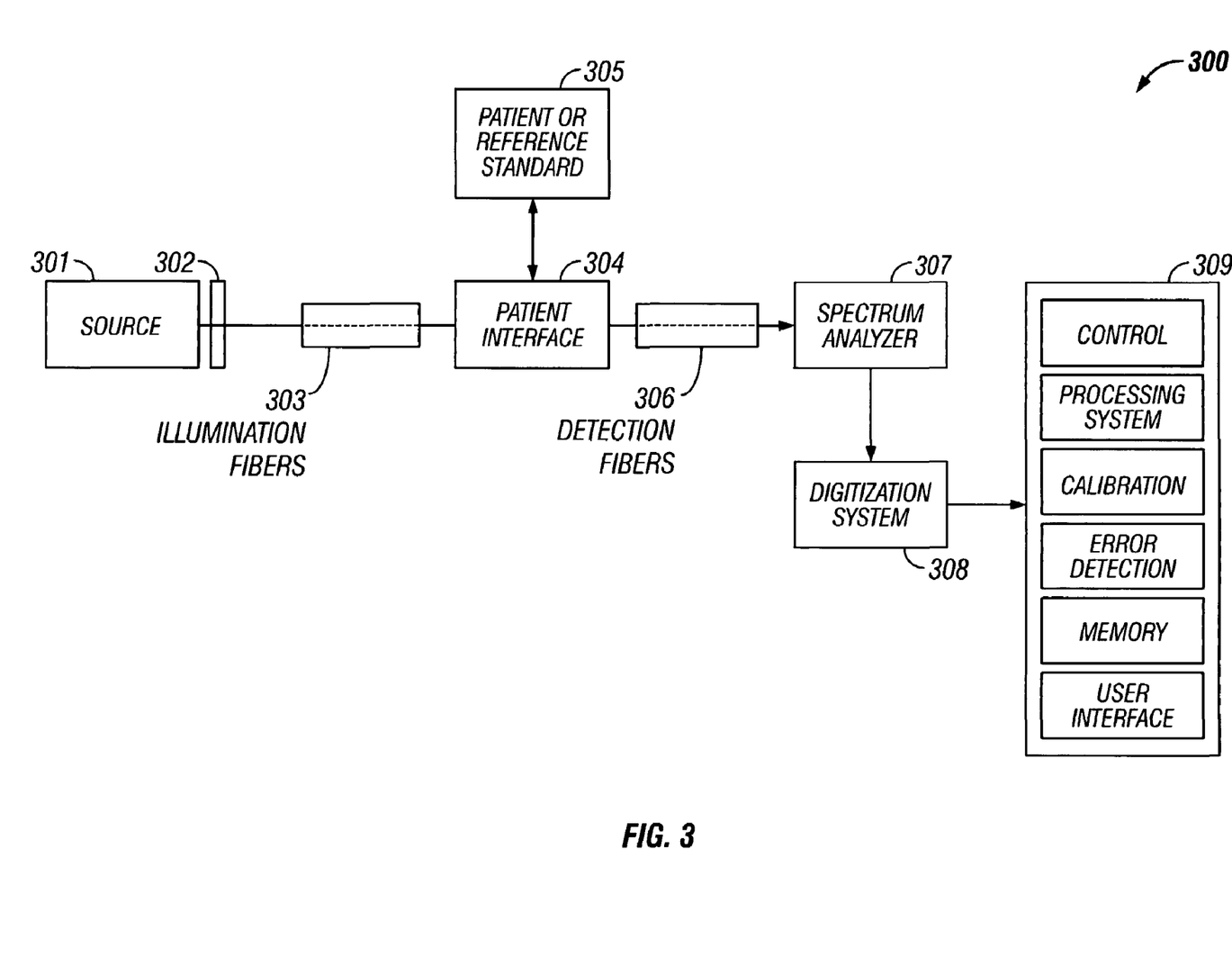
FIG. 3 shows a schematic diagram of an apparatus for noninvasive glucose determination according to the invention.

In the preferred embodiment, local perfusion is monitored spectroscopically and controlled through regulation of the control parameter. The invented method generally includes steps of:

Measuring an analytical signal 101. As shown in FIG. 1, the analytical signal is a near-infrared absorbance spectrum. However, the principles of the invention are applicable to other noninvasive measurement technologies as well. Measurement may be performed using instrumentation as shown in FIG. 3;

The control parameter is measured spectroscopically through application of a first calibration model to the spectral measurement 102, and the value of the parameter relative to the set point 103 is determined;

The relative value of the control parameter is evaluated 104 to determine if it is within the acceptable range about the set point 103;

If the control parameter measurement is acceptable, a glucose calibration 107 is applied to the spectral measurement to produce a glucose measurement;

If the control parameter measurement isn't within an acceptable, an error is generated, and the value is supplied as an input 105 to an element 106 for regulating the control parameter. The loop is repeated, with the control parameter being repeatedly evaluated until the measurement is within the acceptable range.

One embodiment of the above invention provides a method and apparatus for minimizing the confounding effects in a noninvasive spectral measurement attributable to shifts in skin temperature at the tissue measurement site. Near-infrared measurements of skin combined with associated skin temperature reference measurements are used to develop NIR temperature calibrations that require only NIR tissue scans to predict skin surface temperature. Methods of developing calibrations for spectral analysis may employ a variety of multivariate analytical techniques that are well known to those skilled in the art. NIR skin temperature calibration is made possible by the known shifting of the 1450 or 1900 nm water band with variations in skin temperature. The calibration model incorporates the shift information implicitly in the multivariate regression coefficients. Temperature measurement and control of human tissue is important in noninvasive NIR measurement because it provides a means of simplifying the complex overlapping spectral effects that inhibit extraction of the analyte signal. The extra temperature measurement hardware and the associated cost and complexity are avoided by using NIR temperature measurement.

Skin temperature at the measurement site is spectroscopically monitored by calculating temperature values through the application of a multivariate calibration model that correlates spectroscopic changes with shifts in skin temperature. Advantageously, thermal time constants imposed by conventional temperature sensing devices are eliminated, providing near-instantaneous temperature readings. Temperature control may be either active or passive.

Passive control is achieved through the selective application and removal of an occlusive thermal wrap. Active control is provided by a thermistor applied to the skin in the vicinity of the measurement site. Active and passive control may be applied in complementary fashion or they may be used separately. In a particularly preferred embodiment of the invention, the control means is incorporated into the measurement instrument, wherein the calculated skin temperature values provide the feedback in a closed loop that drives the control device. In an alternate embodiment of the invention, the temperature values are supplied to an operator, who then applies active and/or passive control to achieve and maintain a skin temperature within the target range. By monitoring skin temperature spectroscopically and employing methods of passive and/or active control it is possible to reduce the effects of skin temperature variation on the spectral measurement. Active control may be by way of a conductive element, as described above, or it may also be provided by a radiative element.

Non-spectroscopic Control

Figure 2:
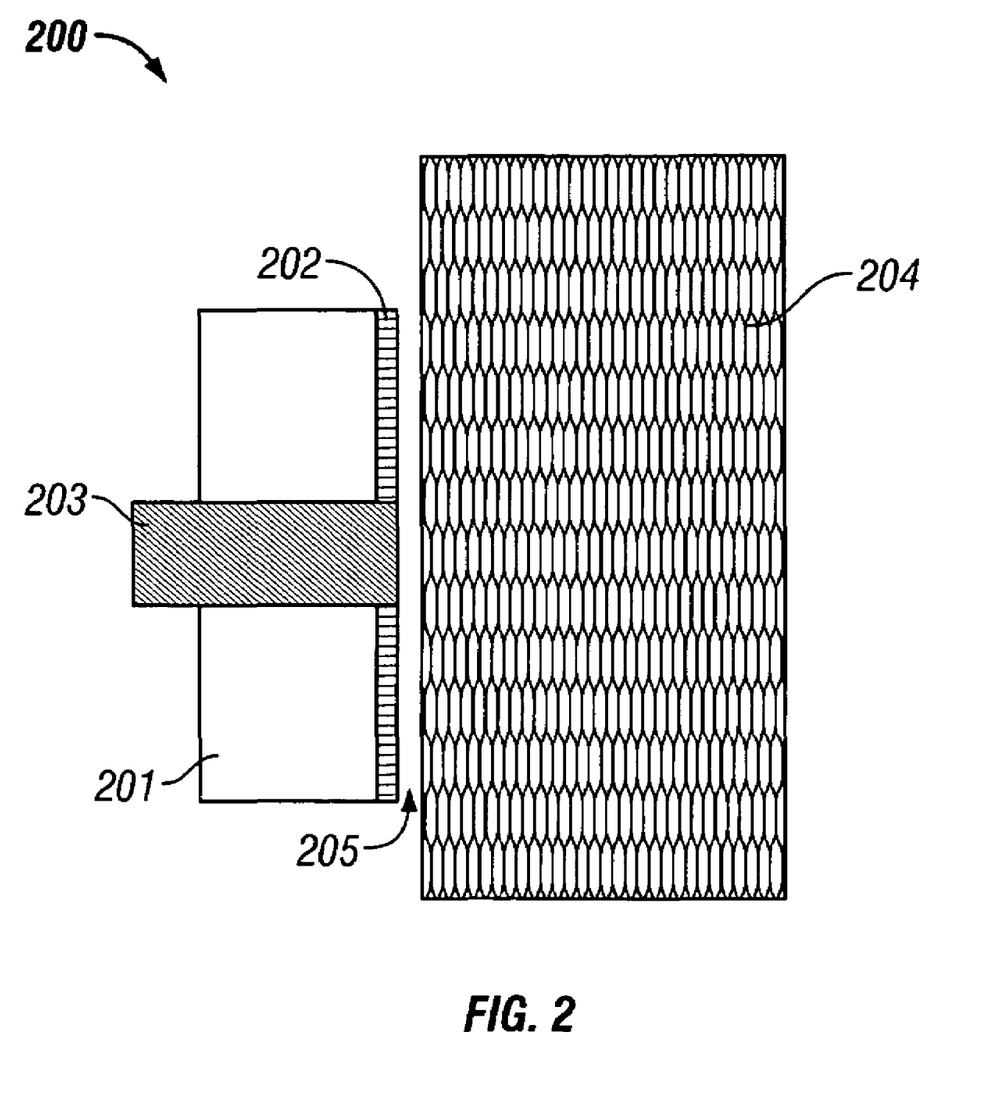
FIG. 2 provides a schematic diagram of a subject interface module according to the invention.

Alternately, perfusion can be controlled in an open-loop fashion by maintaining skin temperature at a specific setpoint, as shown in FIG. 2. The control of skin temperature is performed conductively through heating and cooling element 201 included as part of a patient interface module 200. In one embodiment, the heating and cooling element may be energy transfer pads. Alternately, skin temperature is controlled through radiative energy transfer from an energy source. The system may include means for monitoring the skin temperature at the measurement site either spectroscopically or through a temperature probe (not shown). During use, a noninvasive probe 203 is placed against the skin at the sample site 204. A coupling medium 205 is employed between the patient interface 202 and the tissue 204. The coupling medium serves to facilitate heat transfer between the patient interface 202 and the tissue 204.

Skin Temperature Regulation Using Heated Coupling Medium.

As previously mentioned, the coupling medium itself may serve to control skin temperature at the sampling site. Thus, an embodiment of the invention is possible in which a heated coupling medium provides the thermal energy to maintain the skin of a sampling site at or near a set point. A number of compounds are suitable for use as a coupling medium; for example, silicone oil. Glycerol and mineral oil could also be used, but they are less desirable alternatives, in view of the fact that both materials contain carbon-hydrogen bonds that could interfere with spectroscopic analysis of an analyte such as glucose.

A particularly preferred embodiment of the coupling medium uses a perfluorinated liquid, such as FLUORINERT, either FC-40, having a fluorocarbon chain length of at least twelve carbons or FC-70, having a fluorocarbon chain length of at least fifteen carbons (3M COMPANY, ST. PAUL Minn.). While the FLUORINERT functions to reduce surface reflection variations in the noninvasive measurement, its heat transfer properties are well suited for use as a thermal regulator. Because the FLUORINERT comes into contact with skin at the measurement site, heat can be transferred across the skin if the temperature of the FLUORINERT differs from that of the skin.

Heated FLUORINERT can be used in place of a heated probe with the advantage of reduced power consumption when compared with a temperature controlled metal probe contact surface. The advantage is gained by the rapid heating of small amounts of FLUORINERT just prior to the measurement. Periodic rapid heating saves power over continuous heating of the metal heater contact surface thereby reducing power consumption and lengthening battery life. The use of heated FLUORINERT also allows for the relocation of the heating electronics away from the probe for increased safety. The use of heated FLUORINERT also allows for the heating of the tissue at the measurement site, which is not heated directly by the probe surface heater as it is not in contact with the tissue at the measurement site. During use, a portion of the heated FLUROINERT is disposed between the patient interface of the probe and the skin surface of the measurement site. Alternatively, the coupling fluid may be heated by the source element in embodiments where the source element is in close proximity to the sampling site.

Feature Extraction

Feature extraction is any mathematical transformation that enhances a quality or aspect of the sample measurement for interpretation [see R. Duda, P. Hart, Pattern Classification and Scene Analysis, John Wiley and Sons, New York (1973)]. The general purpose of feature extraction is to concisely represent or enhance any of the structural, chemical physiological, and optical properties of the tissue measurement site that are indirectly related to the target analyte. For the purposes of the invention, a set of features is developed that is indicative of the effect of the target analyte on the probed tissue. The set of features represents or reflects tissue properties or characteristics that change in various ways according to changes in the any of the structural, chemical, physical, and physiological state of the tissue. The changes in tissue state, in turn, are themselves indirectly related to the target analyte. In contrast, current practice is to directly target the signal due to glucose represented in the tissue measurement. In this context, a direct measurement is defined as a measurement based on the signal generated by the analyte during the measurement process.

An indirect measurement is based upon a physical or chemical property or characteristic that is correlated to the target analyte; but in the indirect measurement the analyte is not the direct source of the measured signal. For example, a direct glucose determination may be based upon any of the glucose absorbance bands at approximately 1590, 1730, 2150, and 2272 nm. The glucose absorbance bands are due to C—H and O—H bonds. An indirect glucose determination may be based upon the water absorbance bands centered at approximately 1450, 1900, or 2600 nm. Similarly, an indirect measurement may be based upon absorbance bands centered at approximately 1675, 1715, 1760, 2130, 2250, or 2320 nm for fat or approximately 1180, 1280, 1690, 1730, 2170, or 2285 nm for protein. Another form of indirect measurement would be based upon scattering of light. In the example of noninvasive measurement of glucose through near-infrared spectroscopy, current approaches use the absorption of light due to the glucose molecules present in the sampled tissue volume to make a glucose determination. Conventionally, then, feature extraction is based on the absorbance due to glucose that can be uniquely identified from the background interference. As previously described, isolation of a signal corresponding to an analyte that is present with relatively small absorbances, such as glucose, presents formidable challenges.

In this document, an analysis is referred to as direct if the analyte of interest is probed directly or if the analyte of interest is involved in a chemical reaction that is subsequently probed. For example, in the common glucose oxidase based analysis of glucose, glucose reacts with oxygen in the presence of glucose oxidase to form hydrogen peroxide and gluconolactone. The reaction products may be involved in subsequent reactions. For example hydrogen peroxide may be oxidized in the presence of platinum to form oxygen, $H^+$, and current. The measurement of any reaction component (glucose or oxygen) or product (gluconolactone or hydrogen peroxide) is a termed a direct reading of glucose, herein. Similarly, analysis of subsequent reactions of product such as hydrogen peroxide to current, $H^+$, or oxygen is herein termed a direct measurement. In this document, a direct reading of glucose would also entail any reading in which the electromagnetic signal generated is due to interaction with glucose or a compound of glucose. For example, the fluorescence approach utilized by Sensors for Medicine and Science in which glucose reversibly binds to an indicator molecule and the resulting molecule is probed by fluorescence is herein termed a direct measurement. An "indirect" method of measuring glucose involves the utilization of factors that are affected by the concentration of glucose, such as the fluid distribution in the various tissue compartments. Other terms for an "indirect" reading of this nature include physiologically correlated. correlated response, secondary response, secondary mechanism, glucose induced response, or analyte induced tissue response.

The invention advances the state of current technology through extraction of features that represent changes in the state (physical, chemical and physiological properties or characteristics) of the tissue from a prior state, distinct from the target analyte, in response to changes in the concentration of a target analyte, that occur as represented in the measured changes in tissue properties. For example, a change in glucose concentration triggers a redistribution of fluids between extra-cellular, intra-cellular, extra-vascular, and intra-vascular compartments. The features targeted for extraction, therefore, represent tissue properties related to 1) the concentration of water in each of the compartments, 2) the relative concentration of water in the compartments, 3) the size of the various compartments, 4) the change in electrical impedance resulting from the redistribution of water, and 5) the change in radiation emanating from the tissue.

Subsequently, the features are then applied to identify conditions unsuitable for analyte measurement and/or to perform an actual measurement of a tissue analyte. For example, in the case of noninvasive measurement of glucose through near-infrared spectroscopy, a resolved estimate of the magnitude of the fat band absorbance can be used to infer specific information about the dermis. Although fat is relatively absent from the dermis, near infrared radiation must propagate through the dermis to penetrate the adipose tissue beneath. Thus, physiological changes lead to corresponding changes in the optical properties of the dermis that influence the level of near-infrared radiation that penetrates to and is absorbed by the fat in adipose tissue. Therefore, the magnitude of the fat band present in a near-infrared absorbance spectrum varies, in part, according to the variation in the optical properties of the dermis. For example, as the water concentration in the dermis increases, the detected magnitude of the fat band naturally decreases and vice versa.

Several types of features are determined and optionally used in the remaining steps of the invention:

outlier detection 305; [see T. Ruchti, C. Briggs, T. Blank, A. Lorenz, M. Mattu, M. Makarewicz, An intelligent system for detecting errors and determining failure modes in noninvasive measurement of blood and tissue analytes, U.S. patent application Ser. No. 10/211,478, (Aug. 1, 2002), the entirety of which is hereby incorporated by reference.]

compensation for changes in the properties of tissue 303, 306; and analyte measurement 308.

Given the tissue measurement, m (or the preprocessed measurement, x);

"simple" features are derived directly from the tissue measurement;

additional (derived) features are determined from the simple features through one or more mathematical transformation such as addition. subtraction, division, and multiplication; and abstract features are derived through linear and nonlinear transformations of the tissue measurement.

While simple and derived features generally have a physical interpretation related to the properties of the tissue, such as the magnitude of the fat absorbance, the set of abstract features does not necessarily have a specific interpretation related to the physical system. For example, the scores of a factor analysis, principal component analysis, or partial-least squares decomposition are used as features, although their physical interpretation is not always known. The utility of the principal component analysis is related to the nature of the tissue measurement. The most significant variation in the tissue measurement is not caused directly by glucose but is related to the state, structure, and composition of the measurement site. This variation is modeled by the primary principal components. Therefore, the leading principal components tend to represent variation related to the structural properties and physiological state of the tissue measurement site and, consequently, reflect the tissue properties.

In certain instances, the entire tissue measurement, after suitable preprocessing, is selected within the measurement module for application of a calibration model 307 to estimate the concentration 306 of an analyte.

Instrumentation

While a variety of sensors or instrument configurations are suitable for practice of the invention, FIG. 3 provides a schematic diagram of a preferred embodiment of the sensor. The sensor includes a radiation source such as a tungsten halogen near-infrared radiation source 301, a wavelength selection filter 302 passing light in a range of approximately 1150 to 1850 nm; optional illumination fibers 303 for conveying the source photons to an in-vivo skin sample 204; an interface 200 to the sample site, for example, a patient's forearm; detection fibers 306 for gathering diffusely reflected and transflected radiation from the skin to a spectrum analyzer 307 that includes, for example a grating (not shown), and a detector array (not shown) to detect the radiation; an AD (analog-to-digital) converter 308 for converting the detected signal to a voltage; and processing means 309 for converting the voltage into a glucose concentration.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

The invention claimed is:

1. A noninvasive method of measuring a tissue analyte, comprising steps of:
   controlling skin temperature proximate sampling tissue by applying a coupling medium, said coupling medium comprising a liquid having been pre-heated apart from the tissue;
   collecting an analytical signal from the tissue, said collected signal comprising a tissue measurement;
   extracting at least one feature from the analytical signal indicative of the effect of the target analyte on the probed tissue;
   performing one of: correcting a direct analyte measurement based on said at least one feature, or calculating concentration of said analyte indirectly by application of a calibration model to said at least one feature.

2. The method of claim 1,
   further comprising a step of pre-heating the coupling medium apart from the tissue prior to applying the coupling medium.

3. The method of claim 1, where the step of collecting an analytical signal from the tissue comprises:
   directing near-infrared energy upon the tissue via the coupling medium and measuring one or more properties of infrared energy exiting the tissue.

4. The method of claim 1, the coupling medium comprising one of:
   a perfluorocarbon, or a fluorocarbon.

5. The method of claim 1, wherein said coupling medium comprises any of:
   silicone oil;
   mineral oil; or
   glycerol.

6. The method of claim 1, wherein said coupling medium comprises a perfluorocarbon liquid.

7. The method of claim 6, wherein said perfluorocarbon liquid has a fluorocarbon chain length of at least twelve carbons.

8. The method of claim 7, wherein said perfluorocarbon liquid has a fluorocarbon chain length of at least fifteen carbons.

9. The method of claim 1, wherein skin temperature is controlled to between approximately 30 and 40 degrees centigrade.

10. The method of claim 9, wherein skin temperature is controlled to between approximately 30 and 35 degrees centigrade.

11. The method of claim 1, wherein skin temperature is maintained to within approximately 1 degree centigrade of a set point.

12. The method of claim 11, wherein outermost 100 μm of said skin is controlled to within approximately 1 degree centigrade of a set point.

13. The method of claim 1, wherein said analyte comprises glucose.

14. The method of claim 1, wherein said feature represents redistribution of fluids between at least two of:
   an extra-cellular compartment;
   an intra-cellular compartment;
   an extra-vascular compartment; and
   an intra-vascular compartment.

15. The method of claim 1, wherein said analytical signal comprises an indirect representation of said concentration of said analyte.

16. The method of claim 15, wherein said indirect representation comprises a scattering signal.

17. A noninvasive method of measuring a tissue analyte, comprising acts of:
   stabilizing optical properties of said tissue at a measurement site;
   collecting an analytical signal from the tissue, said collected signal comprising a tissue measurement;
   extracting at least one feature from the analytical signal indicative of the effect of the target analyte on the probed tissue; and
   calculating concentration of said analyte indirectly by application of a calibration model to said feature;
   where the act of stabilizing optical properties comprises controlling skin temperature at the measurement site by performing acts comprising: an operator applying a thermal wrap.

* * * * *